United States Patent
Itsuji et al.

(10) Patent No.: US 7,682,567 B2
(45) Date of Patent: Mar. 23, 2010

(54) SENSOR FOR ANALYZING OR IDENTIFYING PROPERTY OF OBJECT, SENSING APPARATUS USING SAME, AND SENSING METHOD

(75) Inventors: Takeaki Itsuji, Hiratsuka (JP); Shintaro Kasai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 224 days.

(21) Appl. No.: 10/596,825

(22) PCT Filed: Oct. 26, 2005

(86) PCT No.: PCT/JP2005/020050
§ 371 (c)(1),
(2), (4) Date: Jun. 26, 2006

(87) PCT Pub. No.: WO2006/046745
PCT Pub. Date: May 4, 2006

(65) Prior Publication Data
US 2007/0148047 A1    Jun. 28, 2007

(30) Foreign Application Priority Data
Oct. 29, 2004    (JP)    ............... 2004-315839

(51) Int. Cl.
G01N 21/00    (2006.01)
(52) U.S. Cl. .................................. 422/82.11
(58) Field of Classification Search ............... 422/82.11
See application file for complete search history.

(56) References Cited
U.S. PATENT DOCUMENTS

| | | | |
|---|---|---|---|
| 6,078,705 A * | 6/2000 | Neuschafer et al. ............ 385/12 |
| 6,573,737 B1 | 6/2003 | Lyon et al. .................. 324/753 |
| 6,684,686 B2 | 2/2004 | Itsuji et al. |
| 6,777,244 B2 | 8/2004 | Pepper et al. ................ 436/165 |
| 2002/0068018 A1 | 6/2002 | Pepper et al. ............. 422/82.05 |

(Continued)

FOREIGN PATENT DOCUMENTS

DE    102 57 225    4/2004

(Continued)

OTHER PUBLICATIONS

Nagel, M.; Haring Bolivar, P.; Brucherseifer, H.; Kurz, A.; Bosserhoff, A; Buttner, R. "Integrated THz technology for label free genetic diagnotsics." Applied Physics Letters, 2002, 80(1), pp. 154-156.*

(Continued)

Primary Examiner—Walter D Griffin
Assistant Examiner—Bobby Ramdhanie
(74) Attorney, Agent, or Firm—Fitzpatrick, Cella, Harper & Scinto

(57) ABSTRACT

A sensor is provided which comprises a waveguide for allowing an electromagnetic wave to propagate therethrough and disposing an object at a plurality of positions thereof, and a detecting portion for detecting the electromagnetic wave which has interacted with the object at the plurality of positions and propagated through the waveguide, wherein a property of the object is analyzed or identified based on an information obtained from the electromagnetic wave detected by the detecting portion. Thereby, accurate detection can be effected even when the amount of an object is small.

9 Claims, 10 Drawing Sheets

U.S. PATENT DOCUMENTS

2004/0058339 A1 3/2004 Nagel et al. .................... 435/6
2006/0051009 A1 3/2006 Seki et al.

FOREIGN PATENT DOCUMENTS

JP     2001-074647 A      3/2001
WO     WO 0204928 A1 *   1/2002

OTHER PUBLICATIONS

Negami et al, JP2001-074647. Machine Translation into English. Date: Nov. 28, 2008.*

Nagel, et al., "Three-Dimensional Polymer/Metal-Based Resonators for THz-Biosensing," Infrared and Millimeter Waves, 2004 and $12^{th}$ International Conference on Terahertz Electronics, 2004, Conference Digest of the 2004 Joint $29^{th}$ International Conference, pp. 819-820 (Sep. 27, 2004).

Nagel, et al., "Integrated Planar Terahertz Resonators for Femtomolar Sensitivity Label-Free Detection DNA Hybridization," Applied Optics, OSA, Optical Society of America, vol. 41, No. 10, pp. 2074-2078 (Apr. 1, 2002).

Baras, et al., "On-Chip THz Detection of Biomaterials: A Numerical Study," Journal of Biological Physics, vol. 29, No. 2-3, pp. 187-194 (2003).

Stewing, et al., "A New Class of Improved-Efficiency THz Filters for On-Chip Detection of Biomaterials," Microwave and Optical Technology Letters, Wiley USA, vol. 41, No. 2, pp. 79-82 (Apr. 20, 2004).

Nagel, et al., "A Functionalized THz Sensor for Marker-Free DNA Analysis," Physics in Medicine and Biology IOP Publishing UK, vol. 48, No. 2, pp. 3625-3636 (Nov. 21, 2003).

Torosyan, et al., "Application of Narrowband Tunable THz-Radiation for Biomedical Sensing," Annual Meeting of the IEEE Laser & Electro-Optics Society, vol. 1 of 2, pp. 343-344 (Nov. 11, 2002).

Patent Abstracts of Japan, vol. 2000, No. 20, Jul. 10, 2001 (JP-A 2001-074647, Mar. 23, 2001).

Dec. 22, 2005 International Search Report in PCT/JP2005/020050.

Dec. 22, 2005 Written Opinion in PCT/JP2005/020050.

May 10, 2007 International Preliminary Report on Patentability in PCT/JP2005/020050.

* cited by examiner

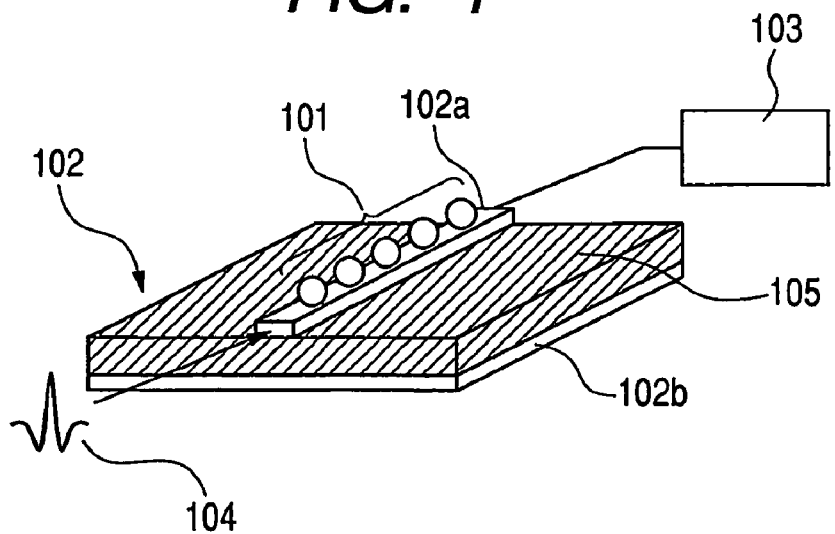
FIG. 1
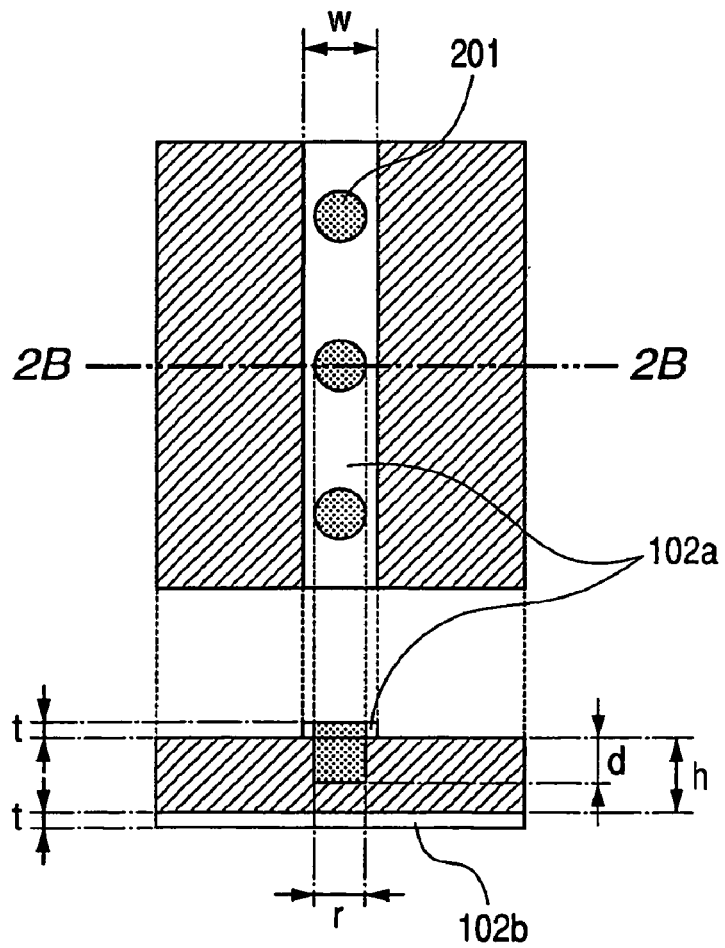
FIG. 2A
FIG. 2B

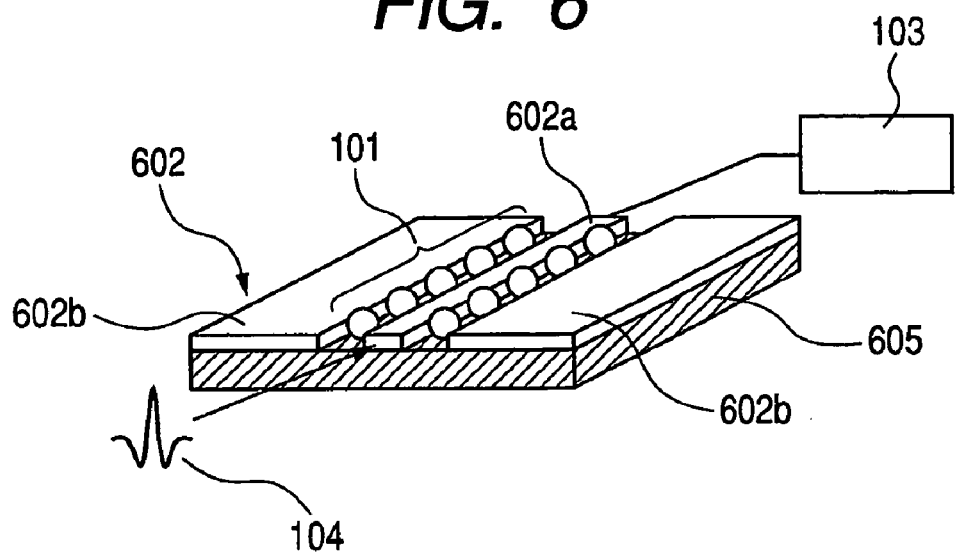
FIG. 6
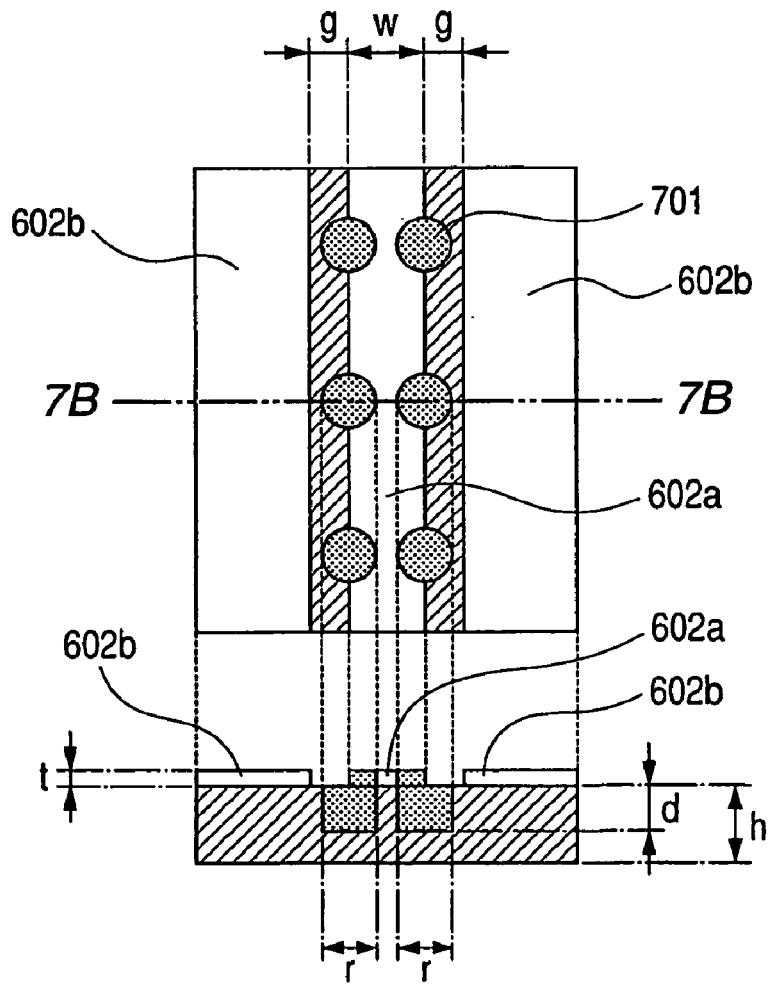
FIG. 7A
FIG. 7B

SENSOR FOR ANALYZING OR IDENTIFYING PROPERTY OF OBJECT, SENSING APPARATUS USING SAME, AND SENSING METHOD

TECHNICAL FIELD

The present invention relates to a sensor for analyzing a property of an object using a high-frequency electromagnetic wave in a millimeter-wave to terahertz-wave region, a sensing apparatus using the sensor, and a sensing method using the sensor. The present invention also relates to a technique for identifying an object based on a property information of the object.

BACKGROUND ART

In recent years, nondestructive inspection techniques using a high-frequency electromagnetic wave of a millimeter-wave to terahertz-wave region (30 GHz to 30 THz) (hereinafter referred to as "terahertz wave") have been under development. Various absorption lines of materials exist in a frequency range of the terahertz wave. Therefore, techniques expected in application fields of an electromagnetic wave of such a frequency band include an imaging technique using a safe fluoroscopic apparatus alternative to an X-ray apparatus, a spectral technique for obtaining an absorption spectrum or complex dielectric constant of a material to examine a bonding state therein, a technique for analyzing biomolecules, a technique for estimating a carrier concentration or mobility.

With respect to the biomolecular analyzing technique using the terahertz wave, there is an application example to a biosensor (Appl. Phys. Lett., Vol. 80, No. 1, p 154-p 156, 2002). As shown in FIGS. 17A, 17B, and 17C, the biosensor is produced by forming a resonance structure in a microstrip line waveguide. When an object (DNA) is applied to the resonance structure portion, the resonance frequency of the waveguide is shifted due to an interaction between the terahertz wave propagating through the waveguide and the object. Here, it is attempted to identify the object based on the amount of shift of the resonance frequency.

A structure in which an object holding portion is provided in a part of an optical waveguide to hold an object is disclosed as a sensor structure for analyzing the object (Japanese Patent Application Laid-Open No. 2001-074647). According to such a sensor, the property of the object is analyzed based on a change in a characteristic of a reflection light propagating through the optical waveguide at a boundary between the object and the optical waveguide. As shown in FIGS. 19A, 19B, and 19C, the object holding portion includes a groove pattern which is extended in a propagation direction and has a predetermined length.

The above-mentioned conventional techniques have the following problems.

FIG. 18 is a cross sectional model view showing a resonance structure portion formed by the method of forming the resonance structure in the waveguide. As shown in FIG. 18, a waveguide 1801 includes conductors 1803 and a ground conductor 1804, each of which is a metallic conductor, and a dielectric 1805 interposed therebetween. An electromagnetic field distribution 1806 in such an arrangement is shown in FIG. 18. Most electromagnetic waves are contained in the dielectric 1085. An object 1802 is analyzed in a region of leak-out of electromagnetic waves caused due to the proximity of the plurality of conductors 1803. As shown in FIG. 18, in order to analyze the object 1802, the object 1802 is applied to the waveguide 1801 so as to cover the entire resonance structure. However, as is seen from FIG. 18, the electromagnetic wave leak-out region, that is, a region in which the object 1802 interacts with the electromagnetic waves, is a minute region, so there is a problem that a part of the object 1802 which does not interact with the electromagnetic waves and is therefore unnecessary is large.

FIGS. 19A, 19B, and 19C are model views showing the sensor structure in which an object holding portion for holding an object is provided in a part of an optical waveguide. As shown in FIGS. 19A and 19B, in a sensor 1, an object 6 is held in an object holding groove 7 and a light is allowed to enter an optical waveguide as indicated by an arrow. The light propagating through the optical waveguide is reflected a plurality of times (two times in FIG. 19C) by the object 6. The object 6 is analyzed based on a change in the characteristic of the reflected light. However, as is also seen from FIG. 19C, the structure shown therein has a problem that a part of the object 6 which is not involved in the reflection of the light propagating through the optical waveguide by the object and is therefore unnecessary is large.

There have been increased demands on sensors for easily analyzing an object at the scene without using a special device and specialized knowledge which have been required up to now, such as an environmental analysis chip for analyzing substances contained in water, an atmosphere, or soil in outdoors scene and a health examination chip for easily performing a health examination at home. For easy analysis, the size of a sensor structure needs to be reduced and the minimum required amount of an object needs to be very small. Therefore, a sensor structure capable of effectively analyzing a small amount of an object has been required. In particular, when a living body is used as an object in the case of a health examination chip for performing a health examination at home, it is desirable that the analysis can be performed effectively with a smaller amount of the object in order to soften the resistance of a user.

DISCLOSURE OF THE INVENTION

Therefore, the present invention provides a sensor comprising a waveguide for allowing an electromagnetic wave to propagate therethrough and disposing an object at a plurality of positions thereof, and a detecting portion for detecting the electromagnetic wave which has interacted with the object at the plurality of positions and propagated through the waveguide, wherein a property of the object is analyzed or identified based on an information obtained from the electromagnetic wave detected by the detecting portion.

In the present invention, the sensor may be provided in plurality on a substrate.

The present invention also provides a sensing apparatus comprising a waveguide for allowing an electromagnetic wave to propagate therethrough and disposing an object at a plurality of positions thereof; a detecting portion for detecting the electromagnetic wave which interacted with the object at the plurality of positions and propagated through the waveguide; a sensor for analyzing or identifying a property of the object based on an information obtained from the electromagnetic wave detected by the detecting portion; and a storage portion for storing an information associated with the property of the object, wherein the information obtained from the electromagnetic wave detected by the detecting portion is compared with the information stored in the storage portion to analyze or identify the property of the object.

The present invention also provides a sensing apparatus comprising a waveguide for allowing an electromagnetic wave to propagate therethrough and disposing an object at a plurality of positions thereof; a detecting portion for detecting the electromagnetic wave which interacted with the object at the plurality of positions and propagated through the waveguide; a sensor for analyzing or identifying a property of the object based on an information obtained from the electromagnetic wave detected by the detecting portion; and means for coupling the electromagnetic wave into the waveguide for allowing the electromagnetic wave to propagate therethrough.

Further, the present invention provides a method comprising the step of disposing an object at a plurality of positions of a waveguide for allowing an electromagnetic wave to propagate therethrough, and the step of detecting the electromagnetic wave which interacted with the object at the plurality of positions and propagated through the waveguide and analyzing or identifying a property of the object based on an information obtained from the detected electromagnetic wave.

In the present invention, a property of an object is analyzed or identified based on a change in a characteristic of an electromagnetic wave, which is caused by the interaction between the electromagnetic wave and the object disposed at a plurality of positions. Thus, the object is disposed at the plurality of positions, so that the object itself is allowed to constitute a resonance structure. Therefore, there is an effect that a large and unnecessary amount of an object is not needed and the property of the object can be efficiently analyzed or identified with a trace amount of the object.

BRIEF DESCRIPTION OF THE DRAWINGS

FIG. 1 is a perspective view schematically showing a structure of a sensing apparatus in accordance with an embodiment and Example 1 of the present invention;

FIG. 2A is a plan view schematically showing a structure of a sensor in accordance with Example 1 of the present invention, and FIG. 2B is a cross-sectional view taken along line 2B-2B in FIG. 2A;

FIG. 6 is a perspective view schematically showing a structure of a sensing apparatus in accordance with an embodiment and Example 2 of the present invention;

FIG. 7A is a plan view schematically showing a structure of a sensor in accordance with Example 2 of the present invention, and FIG. 7B is a cross-sectional view taken along line 7B-7B in FIG. 7A;

BEST MODES FOR CARRYING OUT THE INVENTION

Figure 3:
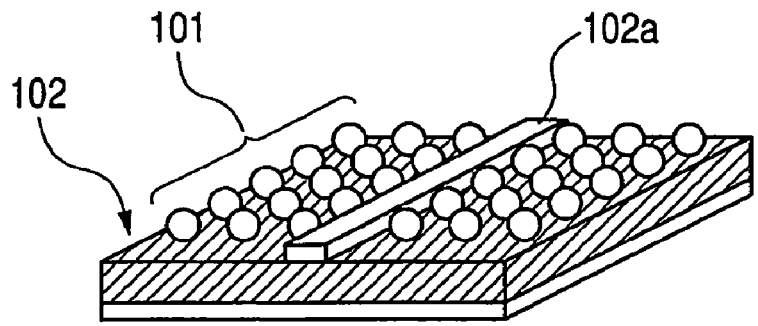
FIG. 3 is a perspective view schematically showing a structure of another example of a sensor in accordance with the present invention.

Hereinafter, best modes for carrying out the present invention will be described with reference to the drawings, wherein like numerals denote like parts FIGS. 1 and 6 are schematic structural views showing sensing apparatuses in accordance with embodiments of the present invention. As shown in the figures, the sensing apparatus in accordance with the present invention includes a waveguide 102, 602 having a structure such that an object 101, which is an inspected object, can be disposed thereon and an electromagnetic wave 104 of a desirable frequency characteristic can propagate therethrough, and an electromagnetic wave detecting portion 103 for detecting the electromagnetic wave 104 propagating through the waveguides 102, 602 to analyze or identify the object 101. Therefore, it is desirable that the electromagnetic wave detecting portion 103 includes an object information reference portion in which a reference information of the object 101 is stored in advance.

It is preferable that the object 101 is periodically disposed by means of an object disposing means on the waveguide 102, 602 at intervals of a wavelength order of the used electromagnetic wave 104. It is more preferable that the object 101 is located on the waveguide 102, 602 at positions on which an electromagnetic field distribution is concentrated. Thus, the object 101 is periodically disposed on the waveguide 102, 602 to form the sensor.

The periodic disposition is not essential, but it is sufficient that the object be disposed at a plurality of positions, and that the disposed object be located at such positions as to allow the object to interact with the electromagnetic wave.

The sensor in accordance with the present invention utilize a phenomenon that by disposing the object 101 at positions on which the electromagnetic field distribution is concentrated, the specific physical characteristics of the object 101 (such as refractive index, attenuation characteristic, and diffraction characteristic) interact with the electromagnetic wave 104 that propagates through the waveguide 102, 602 to thereby change a propagation characteristic of the electromagnetic wave 104. In particular, by disposing the object 101 periodically on the waveguide 102, 602, it is possible to allow an interaction between the object 101 and the electromagnetic wave 104 to occur periodically, thereby producing a specific resonance structure derived from a photonic band gap.

In a sensing apparatus in accordance with one embodiment of the present invention, a change in a characteristic such as phase, intensity or frequency spectrum of the electromagnetic wave 104 propagating through such a resonance structure portion is detected by the electromagnetic wave detecting portion 103 to thereby analyze or identify the property (or specific physical characteristic) of the object 101. The resonance structure efficiently confines the electromagnetic wave 104 and is suitable for high-sensitivity measurement at a specific frequency. Further, when the disposition (or distribution) state of the object 101 is controlled such that the resonance frequency of the resonance structure is in the vicinity of an electromagnetic wave absorption wavelength of the object 101, the electromagnetic wave 104 propagating through the waveguide 102, 602 is significantly influenced by the physical characteristic of the object 101 in addition to receiving the electromagnetic wave confinement effect, so that the properties of the object can be analyzed or identified with a higher sensitivity.

The frequency band of the electromagnetic wave 104 used in the present invention is preferably within a millimeter-wave to terahertz-wave region (30 GHz to 30 THz). Such a frequency band includes absorption wavelengths of various biomolecules, so that when, for example, biomolecules such as proteins are used as the object 101, a high-sensitivity biosensor and biosensing apparatus can be provided.

The structure of the waveguide 102, 602 can be arbitrarily designed as long as the electromagnetic wave 104 of a wavelength within the millimeter-wave to terahertz-wave region can propagate therethrough. In the embodiment of FIG. 1 a microstrip line is used as the waveguide 102, while a co-planar waveguide structure is used in the embodiment of FIG. 6, but other waveguide structures can be also used.

Figure 16:
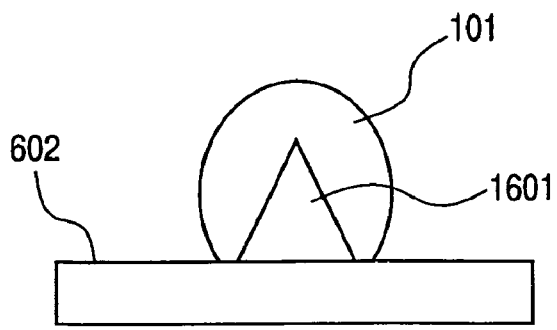
FIG. 16 is a view schematically showing a structure of an example of an object disposing means used in the present invention.
Figure 17A:
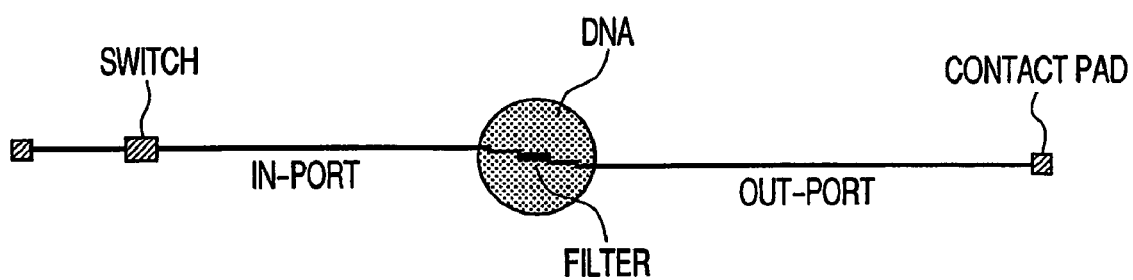
FIGS. 17A, 17B, and 17C are views schematically showing a structure of a conventional sensor.
Figure 17B:
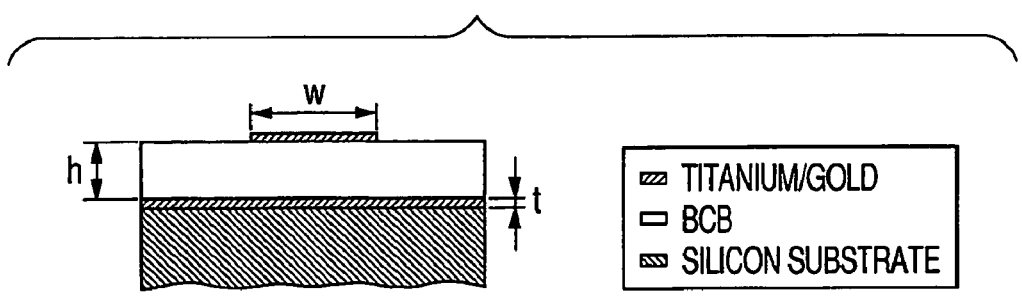
Figure 17C:
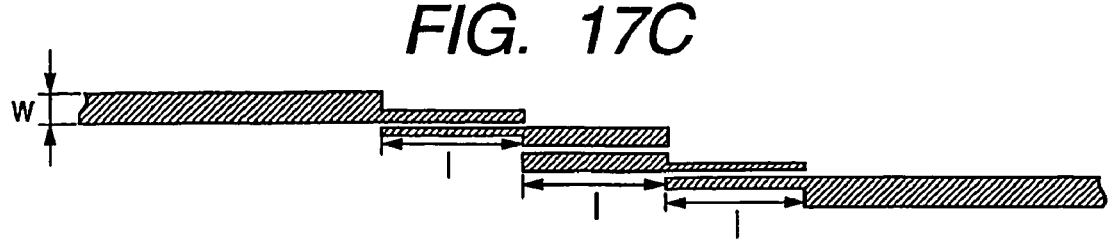
Figure 18:
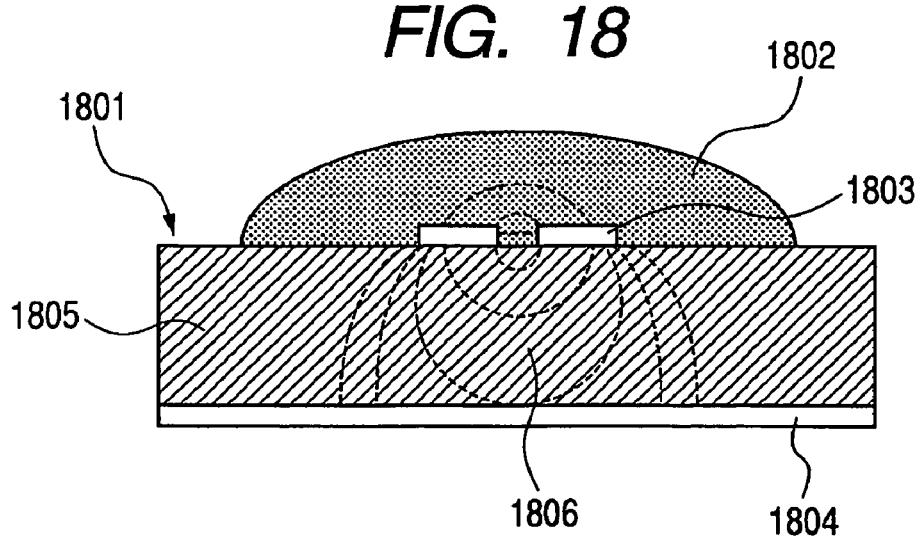
FIG. 18 is cross-sectional view explaining an operation of the conventional sensor.
Figure 19A:
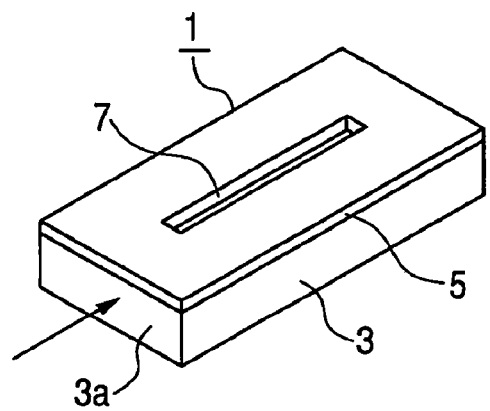
FIGS. 19A, 19B, and 19C are a perspective view and cross-sectional views showing a structure of a conventional sensor.
Figure 19B:
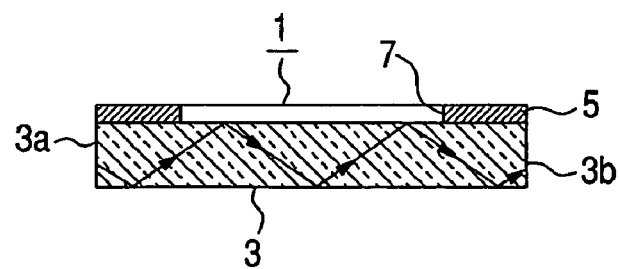
Figure 19C:
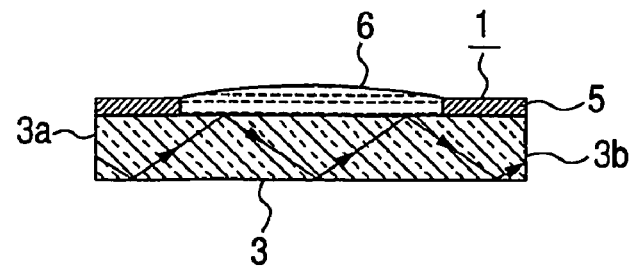

The object disposing means for disposing the object 101 may either be separate from the sensor and provided in the sensing apparatus or be formed in the sensor structure, with a combination thereof being available. In the case of the sensing apparatus for analyzing biomolecules, it is necessary to control the disposition of the object 101, which constitutes the sensor, at an order of several 10 μm to several 100 μm. Specifically, the object is periodically disposed preferably at a pitch corresponding to about a half of a wavelength $\lambda$ of the electromagnetic wave which serves as an inspecting means. It is to be noted that $\lambda$ represents an effective wavelength of the propagating electromagnetic wave. Therefore, for example, the sensing apparatus in accordance with the embodiment includes a structure for ejecting the object 101 onto the waveguide 102, 602 using an inkjet system as the object disposing means. Further, in order to efficiently dispose the object 101 on the waveguide 102, 602, a disposing pattern may be provided on the waveguide 102, 602 which constitutes the sensor. For example, hole(s) or groove(s) are provided in the waveguide 102, 602 or a protrusion shape 1601 such as shown in FIG. 16 is provided, thereby effectively disposing the object 101 by a boundary effect. Incidentally, the protrusion shape 1601 may be formed either of the same dielectric as that constitutes the waveguide 102, 602, or of a conductor. Moreover, it is also possible to form a pattern consisting of a hydrophilic portion and a hydrophobic portion on the waveguide 102, 602 by using a hydrophilic material and a hydrophobic material and dispose the object 101 through a boundary effect thereof. As described above, the object disposing means may be used either singly or in combination. Further, instead of directly and periodically disposing a small amount of the object 101 as in the case of the inkjet system, the object can be disposed in a self-organizing manner by utilizing only a boundary effect. It is desirable that the positions at which the object 101 is disposed are within a region of the waveguide 102 in which an electromagnetic field is strongly distributed.

Figure 4:
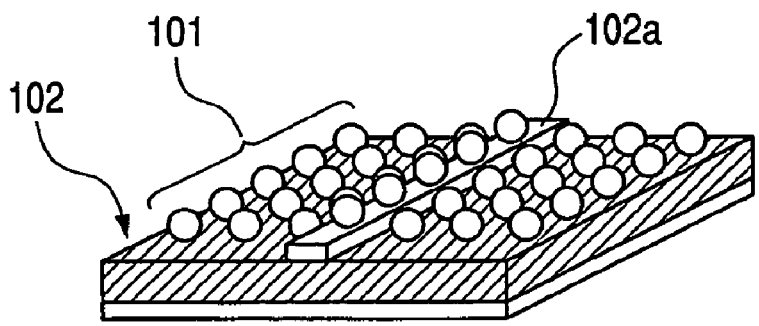
FIG. 4 is a perspective view schematically showing a structure of still another example of a sensor in accordance with the present invention.
Figure 5:
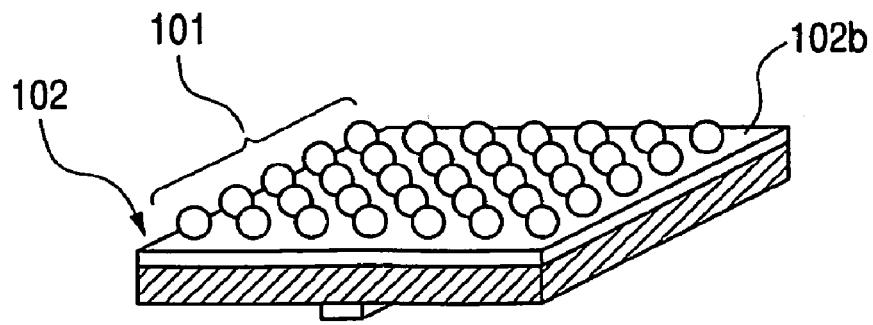
FIG. 5 is a perspective view schematically showing a structure of yet another example of a sensor in accordance with the present invention.

The sensing apparatus shown in FIG. 1 has a sensor structure in which the microstrip line is used as the waveguide 102 and the object 101 is disposed on a conductor 102a at a pitch corresponding to a half of an absorption wavelength $\lambda$. However, the positions at which the object 101 is disposed are not limited to such positions, and a structure in which the object is disposed on both sides of the conductor 102a as shown in FIG. 3, a structure in which the object is disposed on the conductor 102a and on both sides of the conductor 102a as shown in FIG. 4, or a structure in which the object is disposed on a ground conductor 102b as shown in FIG. 5 may also be adopted. It is preferable that the object 101 is disposed at positions of the waveguide 102 at which an electromagnetic field is strongly distributed.

Figure 8:
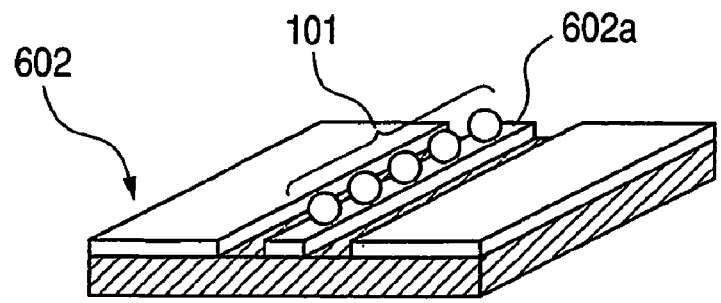
FIG. 8 is a perspective view schematically showing a structure of another example of a sensor in accordance with the present invention.
Figure 9:
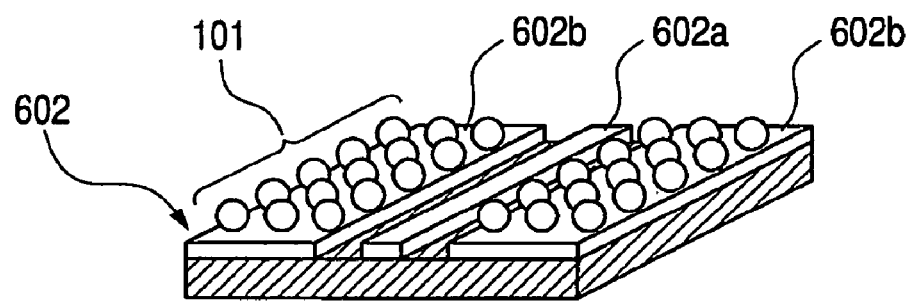
FIG. 9 is a perspective view schematically showing a structure of still another example of a sensor in accordance with the present invention.
Figure 10:
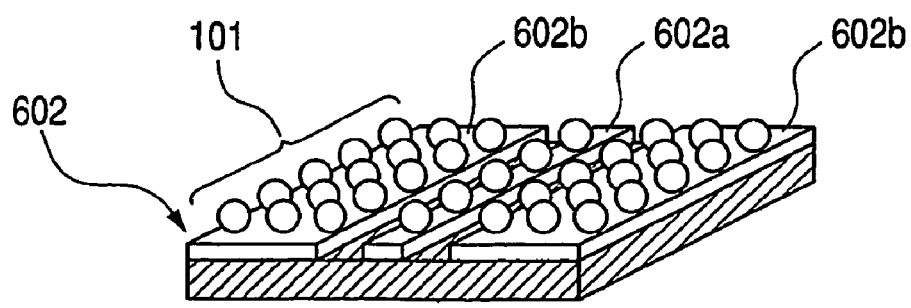
FIG. 10 is a perspective view schematically showing a structure of yet another example of a sensor in accordance with the present invention.
Figure 11:
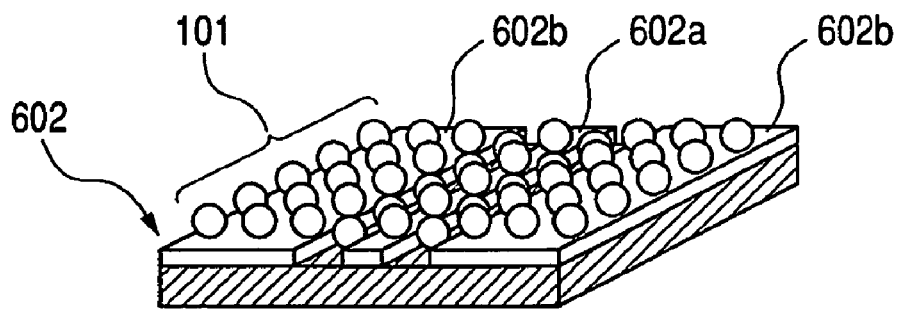
FIG. 11 is a perspective view schematically showing a structure of yet still another example of a sensor in accordance with the present invention.
Figure 12:
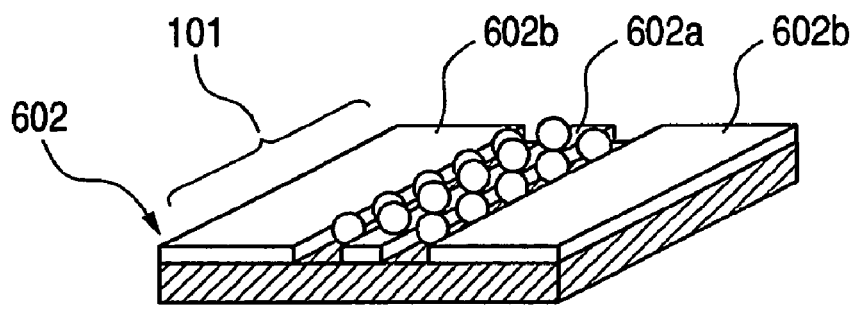
FIG. 12 is a perspective view schematically showing a structure of still another example of a sensor in accordance with the present invention.
Figure 13:
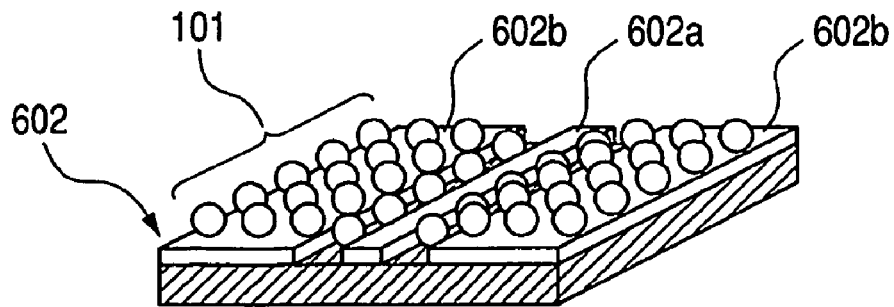
FIG. 13 is a perspective view schematically showing a structure of yet another example of a sensor in accordance with the present invention.

Further, a sensing apparatus shown in FIG. 6 has a sensor structure in which a co-planar waveguide is used as the waveguide 602 and the object 101 is disposed in minute gaps between the conductor 602a and the ground conductors 602b at a pitch corresponding to a half of an absorption wavelength $\lambda$. However, the positions at which the object 101 is disposed are not limited to such positions, and there may also be adopted, for example, a structure in which the object is disposed on the conductor 602a as shown in FIG. 8, a structure in which the object is disposed on the ground conductors 602b as shown in FIG. 9, a structure in which the object is disposed on the conductor 602a and on the ground conductors 602b as shown in FIG. 10, a structure in which the object is disposed on the conductor 602a and on the ground conductors 602b and in minute gaps between the conductor 602a and the ground conductors 602b as shown in FIG. 11, a structure in which the object is disposed in minute gaps between the conductor 602a and the ground conductors 602b and on the conductor 602a as shown in FIG. 12, or a structure in which the object is disposed in minute gaps between the conductor 602a and the ground conductors 602b and on the ground conductors 602b as shown in FIG. 13. It is preferable that the object 101 is disposed at positions of the waveguide 602 at which an electromagnetic field is strongly distributed.

Further, examples of the method of coupling an electromagnetic wave into such sensor structure include a method of using an optical switch and irradiating a gap provided in a part of a waveguide with an ultrashort-pulse light to generate an electromagnetic wave having a desired frequency spectrum, a method of connecting an active element for generating a desired electromagnetic wave to a part of a waveguide, a method of connecting a waveguide to an external circuit through which an electromagnetic wave propagates by means of a connector, and a method of coupling an electromagnetic wave propagating outside into a waveguide by means of an antenna. Alternatively, coupling may be made by using a diffraction grating or a similar element or by utilizing a surface plasmon resonance technique. However, the present invention is not limited to use of these methods and includes use of any method or means capable of coupling an electromagnetic wave having a desired frequency spectrum into the sensor structure in accordance with the present invention.

According to the sensing apparatus of the present invention, by changing a frequency spectrum through an interaction with an object and analyzing a change in the frequency spectrum detected by an electromagnetic wave detecting portion, it is possible to analyze or identify a property of the object

EXAMPLES

Example 1

An example of application of the sensing apparatus in accordance with the present invention to a biochemical sensor will be described below. Incidentally, in the following description, the numerical values to respective portions of the sensors in accordance with the examples are given for purposes of illustration only and are not intended to be limiting of the invention.

FIG. 1 is a perspective view schematically showing a structure of a sensing apparatus in accordance with this example.

As shown in the figure, a sensor which constitutes a sensing apparatus in accordance with this example comprises a waveguide 102 of a microstrip line type consisting of a conductor 102a, a ground conductor 102b, and a dielectric 105. In the figure, reference numeral 101 denotes an object to be analyzed or identified. Further, in this example, as the method of coupling an electromagnetic wave 104 into the waveguide 102, an antenna structure which is not shown is provided at a part of the waveguide 102. However, the present invention is not limited to use of such method, and, as described above, a method of connecting an active element for generating a desired electromagnetic wave to a part of a waveguide or a method of connecting a waveguide to an external circuit through which an electromagnetic wave propagates by means of a connector may also be used. Alternatively, coupling may be made by using a diffraction grating or a similar element or by utilizing a surface plasmon resonance technique.

In this example, BCB (benzocyclobutene; dielectric constant: 2.4) is used for the dielectric 105. Further, a stack of Ti and Au is used for the conductor 102a and the ground conductor 102b. However, the present invention is not limited to use of such materials, and a material having a low loss in a high-frequency band, such as polyimide or polysilane, or a semiconductor material such as GaAs or Si may be used as a material of the dielectric, while the material of the conductors is suitably selected in consideration of a loss of a electromagnetic wave, adhesive properties to the dielectric material at the time of processing, easiness of processing, and the like.

FIG. 2A is a plan view schematically showing a structure of a sensor in accordance this example; and FIG. 2B is a cross-sectional view taken along line 2B-2B in FIG. 2A. As shown in the figure, in the sensor in accordance with this example, holes 201 as a means for disposing the object 101 are periodically provided in the waveguide 102. In the waveguide 102, the dielectric 105 having a dielectric thickness h of 5 μm is interposed between the conductor 102a and the ground conductor 102b, each of which has a conductor thickness t of 300 nm. Because the holes 201 are provided, an electromagnetic field is distributed strongly inside of the dielectric 105, thereby making it possible to cause a stronger interaction between the electromagnetic wave 104 and the object 101. When a conductor width w of the conductor 102a is set to 13.5 μm, the waveguide 102 functions as a waveguide having a characteristic impedance of 50Ω. As the method of disposing the object 101, for example, the object 101 is ejected into the holes 201 by use of an inkjet system. However, as described above, the present invention is not limited to use of such a method. The holes 201 are arranged at intervals corresponding to the disposition interval of the object. In this example, as a model for analysis described below, the holes 201 were arranged at an interval of 50 μm, a hole diameter r thereof was set to 10 μm, and a depth d of the hole 201 was set to 3 μm. However, these values are given for purposes of illustration only and are not intended to be limiting of the invention. At this time, a photonic bandgap which selectively inhibits the propagation of an electromagnetic wave of a frequency in the vicinity of 2 THz was developed in the waveguide 102. The above processing was performed using a known process technique. The above parameter values are not limitative and vary as needed depending on a frequency at which the photonic bandgap is develops or matchability with other peripheral circuits.

Figure 23:
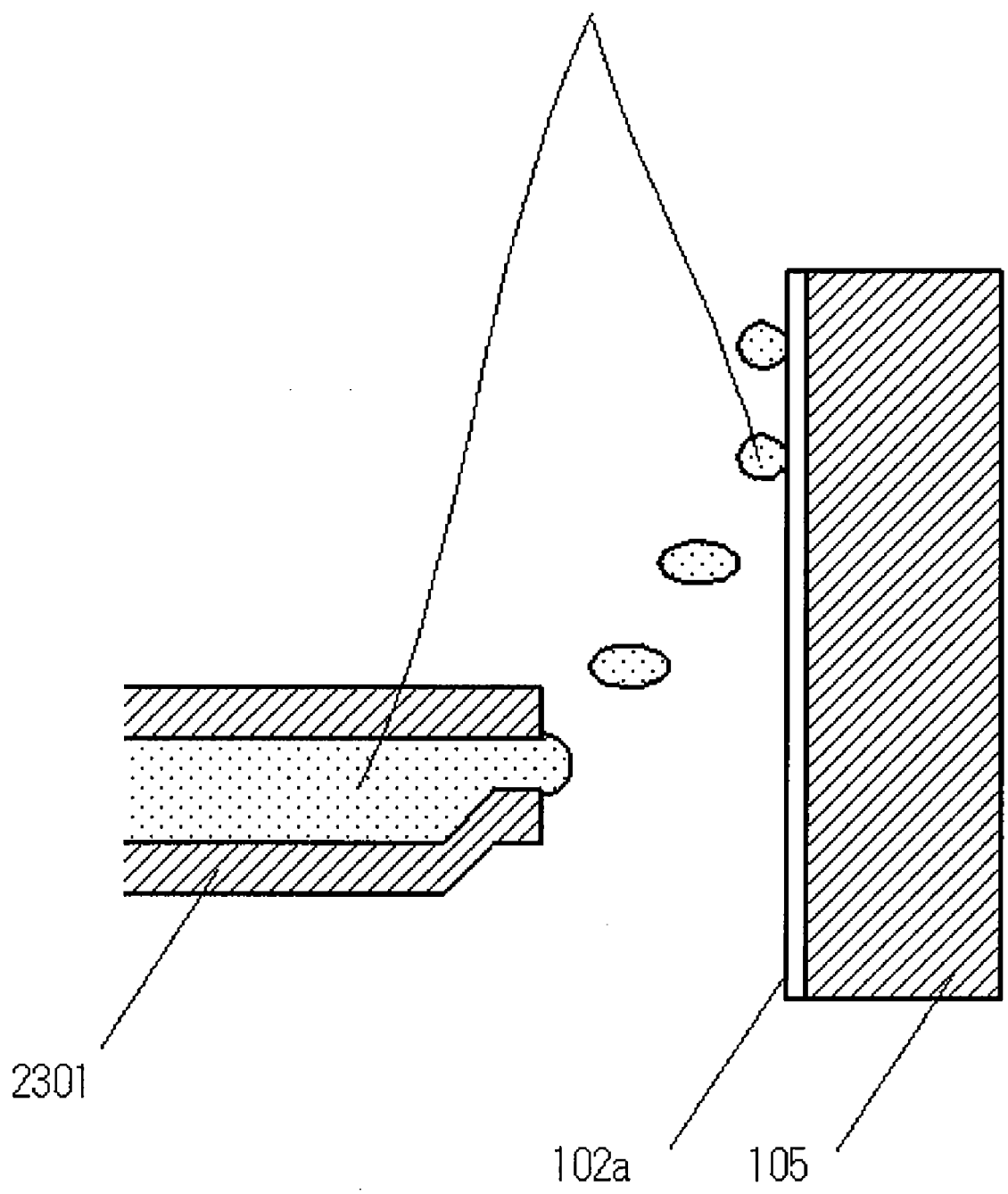
FIG. 23 is a perspective view of an inkjet system in accordance with example embodiments of the invention.

FIG. 23 shows an example embodiment of an inkjet system that may be used in accordance with example embodiments of the invention. As discussed above, the inkjet 2301 ejects objects 101 towards the conductor 102a.

Figure 14:
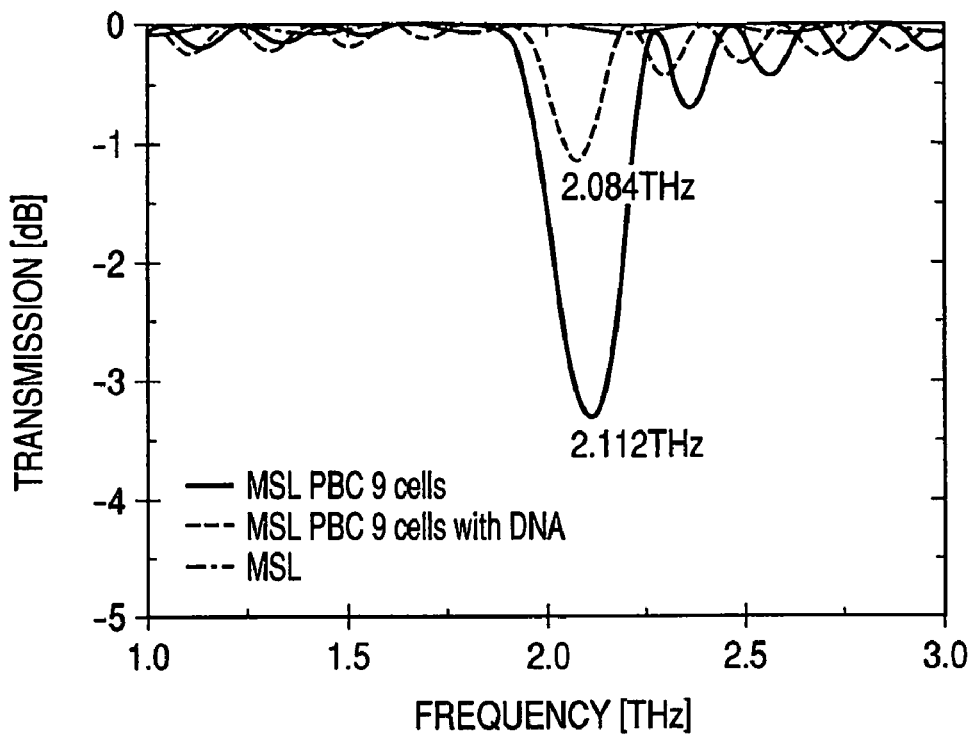
FIG. 14 is a graphical representation showing an analysis result of the sensor in accordance with Example 1.

FIG. 14 shows an analysis example with respect to the operation of the sensor in which the object 101 is disposed on the waveguide 102. Here, the analysis was carried out using a structure in which the object 101, which was a DNA having a dielectric constant of 4.0, was periodically disposed at nine points. As shown in the figure, when the DNA is not disposed, a resonance frequency exists in the vicinity of 2.1 THz as indicated by a solid line. However, when the DNA is disposed, it is determined that the resonance frequency shifts to a lower frequency side by 1.3% as indicated by a broken line. Further, the signal is attenuated by about 2 dB. For example, when the above information is compared with a frequency spectrum of the electromagnetic wave 104 propagating through the sensor in the sensing apparatus shown in FIG. 1, the object 101 can be analyzed or identified. In this analysis, only the dielectric constant of the objects 101 is considered. However, when a specific attenuation characteristic or specific diffraction characteristic of the object 101 is further considered, there is a possibility that the shift amount, the attenuation amount, or the change in the amount of frequency spectrum may become significant. Therefore, by using such information to sense the object 101, more detailed analysis or identification becomes possible.

Further, when a dielectric attaches to a high-frequency circuit, the propagation state of an electromagnetic wave varies, so that the circuit cannot be generally disposed in a position at which an object exists. In the present invention, because the structure in which the object is periodically disposed in the vicinity of a waveguide is adopted, it is unnecessary to apply an object to a large region including a resonance structure, unlike the conventional example. Therefore, other high-frequency circuits which constitute a sensor can be integrated, thereby easily reducing the size of the sensor.

Further, in the present invention, because it is only necessary to periodically dispose an object in the vicinity of a waveguide, a resonance structure does not need to be necessarily produced on the waveguide, so that the property of the object can be detected only by disposing the object at arbitrary positions in the vicinity of the waveguide. Thus, there is obtained an effect that the degree of freedom of layout of circuits which constitute the sensor increases.

Further, in the present invention, because the structure in which an object is periodically disposed in the vicinity of a waveguide is adopted, the pieces of object which exist in the vicinity of the waveguide can be maintained at a suitable height by an effect of a boundary between the object and the waveguide. Therefore, because a region in which the object and the electromagnetic wave interact with each other is enlarged, there is obtained an effect that the properties of the object can easily be analyzed or identified with a high accuracy.

Example 2

An example of application of the sensing apparatus in accordance with the present invention to a biochemical sensor will be described below. Incidentally, in the following description, the numerical values to respective portions of the sensors in accordance with the examples are given for purposes of illustration only and are not intended to be limiting of the invention.

FIG. 6 is a perspective view schematically showing a structure of a sensing apparatus in accordance with this example.

As shown in the figure, a sensor which constitutes a sensing apparatus in accordance with this example comprises a waveguide 602 of a co-planar type consisting of a conductor 602a, two ground conductors 602b, and a dielectric 605. In the figure, reference numeral 101 denotes an object to be analyzed or identified. Further, in this example, as the method of coupling an electromagnetic wave 104 into the waveguide 602, an antenna structure which is not shown is provided at a part of the waveguide 602. However, the present invention is not limited to use of such method, and, as described above, a method of connecting an active element for generating a desired electromagnetic wave to a part of a waveguide or a method of connecting a waveguide to an external circuit through which an electromagnetic wave propagates by means of a connector may also be used. Alternatively, coupling may be made by using a diffraction grating or a similar element or by utilizing a surface plasmon resonance technique.

In this example, BCB (benzocyclobutene; dielectric constant: 2.4) is used for the dielectric 605. Further, a stack of Ti and Au is used for the conductor 602a and the two ground conductors 102b. However, the present invention is not limited to use of such materials, and a material having a low loss in a high-frequency band, such as polyimide or polysilane, or a semiconductor material such as GaAs or Si may be used as a material of the dielectric, while the material of the conductors is suitably selected in consideration of a loss of a electromagnetic wave, adhesive properties to the dielectric material at the time of processing, easiness of processing, and the like.

FIG. 7A is a plan view schematically showing a structure of a sensor in accordance this example; and FIG. 7B is a cross-sectional view taken along line 7B-7B in FIG. 7A. As shown in the figure, in the sensor in accordance with this example, holes 701 as a means for disposing the object 101 are periodically provided in the waveguide 602. In the waveguide 602, the conductor 602a having a conductor thickness t of 300 nm and the ground conductors 602b each having a conductor thickness t of 300 nm and located on both sides of the conductor 602a at given intervals g from the conductor 602a are formed on the dielectric 105 having a dielectric thickness h of 5 μm. Therefore, an electromagnetic field is distributed strongly between the conductor 602a and the ground conductors 602b which are located at the given intervals g, and when the object 101 is periodically disposed at such locations, the electromagnetic wave 104 and the object 101 interact with each other. In this example, in order to more surely achieve the periodic disposition of the object 101, the holes 701 are used. When a conductor width w of the conductor 602a is set to 13.5 μm and the intervals g between the conductor 602a and the ground conductors 602b are set to 2.5 μm, the waveguide 102 functions as a waveguide having a characteristic impedance of 50Ω. As the method of disposing the object 101, for example, the object 101 is ejected into the holes 701 by use of an inkjet system. However, as described above, the present invention is not limited to use of such a method. The holes 701 are arranged at intervals corresponding to the disposition interval of the object. In this example, as a model for analysis described below, the holes 701 were arranged at an interval of 50 μm, a hole diameter r thereof was set to 10 μm, and a depth d of the hole 701 was set to 3 μm. However, these values are given for purposes of illustration only and are not intended to be limiting of the invention. At this time, a photonic bandgap which selectively inhibits the propagation of an electromagnetic wave of a frequency in the vicinity of 2 THz was developed in the waveguide 602. The above processing was performed using a known process technique. The above parameter values are not limitative and vary as needed depending on a frequency at which the photonic bandgap is develops or matchability with other peripheral circuits.

Figure 15:
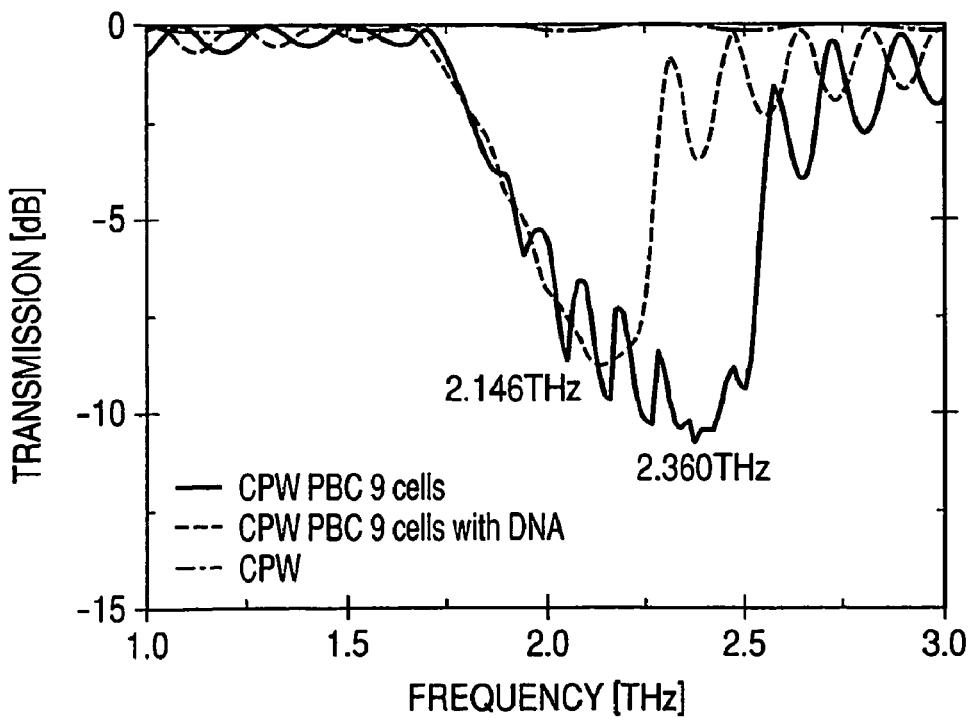
FIG. 15 is a graphical representation showing an analysis result of the sensor in accordance with Example 2.

FIG. 15 shows an analysis example with respect to the operation of the sensor in which the object 101 is disposed on the waveguide 602. Here, the analysis was carried out using a structure in which the object 101, which was a DNA having a dielectric constant of 4.0, was periodically disposed at nine points. As shown in the figure, when the DNA is not disposed, a resonance frequency exists in the vicinity of 2.4 THz as indicated by a solid line. However, when the DNA is disposed, it is determined that the resonance frequency shifts to a lower frequency side by 9.0% as indicated by a broken line. Further, the signal is attenuated by about 2 dB. For example, when the above information is compared with a frequency spectrum of the electromagnetic wave 104 propagating through the sensor in the sensing apparatus shown in FIG. 6, the object 101 can be analyzed or identified. In this analysis, the structure in which the holes 702 are provided between the conductor 602a and the ground conductors 602b is adopted. However, it has been determined that even when the holes 702 are not provided, a change of the same degree as above occurs in the frequency spectrum. Further, in this analysis, only the dielectric constant of the objects 101 is considered. However, when a specific attenuation characteristic or specific diffraction characteristic of the object 101 is further considered, there is a possibility that the shift amount, the attenuation amount, or the change in the amount of frequency spectrum may become significant. Therefore, by using such information to sense the object 101, more detailed analysis or identification becomes possible.

Example 3

Figure 20:
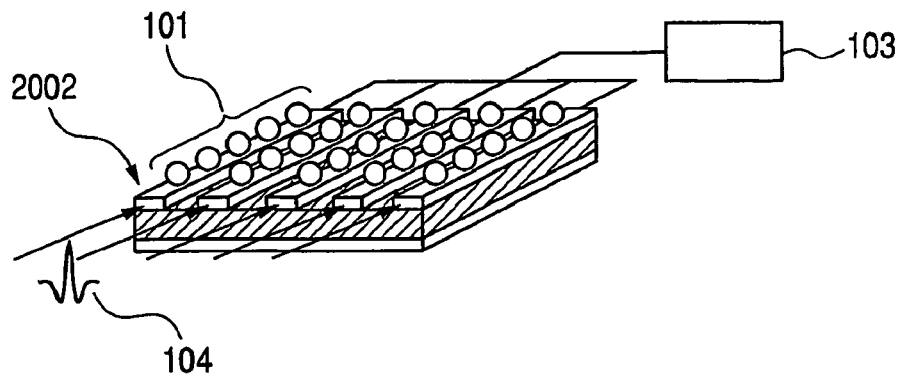
FIG. 20 is a perspective view schematically showing a structure of a sensing apparatus in accordance with Example 3 of the present invention.

A structural example of a sensor of a sensing apparatus in accordance with the present invention will be described below. As shown in FIG. 20, the structure of a sensor in accordance with this example is constituted of an array of the above-described sensor. In the sensor in accordance with the present invention, because the object 101 is disposed by the object disposing means, the state of the disposition can be controlled. FIG. 20 shows an example of the structure of a sensor array 2002 in which a plural number of the microstrip line sensor structures described in Example 1 are arrayed. As described above, the sensor structure is not limited to such a structure. Further, in this example, as the method of coupling an electromagnetic wave 104 into the waveguide, an antenna structure which is not shown is provided at a part of the waveguide. However, the present invention is not limited to use of such method, and, as described above, a method of connecting an active element for generating a desired electromagnetic wave to a part of a waveguide or a method of connecting a waveguide to an external circuit through which an electromagnetic wave propagates by means of a connector may also be used. Alternatively, coupling may be made by using a diffraction grating or a similar element or by utilizing a surface plasmon resonance technique.

The sensor in accordance with the present invention is produced by using, as the object disposing method, the method of mechanically controlling the disposition state of the object 101 by means of an inkjet system or the like, or the method of utilizing an effect of a boundary through formation of holes or protrusions or patterning using a hydrophilic and a hydrophobic materials. Therefore, the object 101 is difficult to be spread, so that there is obtained an advantage that sensors can be provided close to each other. Further, because the disposition state of the object 101 can be freely controlled, when the disposition state is changed for each of the sensor parts constituting the sensor array 2002, plural kinds of objects 101 can be simultaneously analyzed or identified, or a plurality of materials constituting an objects 101 can be simultaneously analyzed or identified. Therefore, with the sensor of the sensing apparatus in accordance with the present invention, a plurality of sensors can be easily integrated close to each other by the object disposing means. Therefore, plural kinds of information can be simultaneously obtained, so that there is obtained an advantage that a time required for analysis or identification can be significantly shortened.

Example 4

An example of application of the sensing apparatus in accordance with the present invention to a biochemical sensor will be described below. Incidentally, in the following description, the numerical values to respective portions of the sensors in accordance with the examples are given for purposes of illustration only and are not intended to be limiting of the invention. The above-described sensors each have the structure in which the object is periodically disposed. In contrast thereto, this example is featured by that the object is discretely disposed at a plurality of positions.

Figure 21:
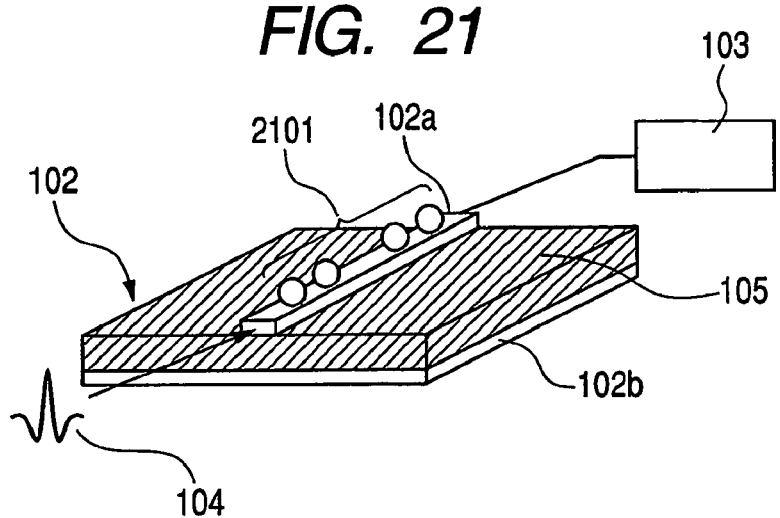
FIG. 21 is a perspective view schematically showing a structure of a sensing apparatus in accordance with Example 4 of the present invention.

FIG. 21 shows a sensor structure in accordance with this example. The sensor structure in accordance with this example is basically identical to the microstrip line structure described in Example 1. However, in this example, because it is only necessary to discretely dispose the object, the sensor structure is not limited thereto, as described above. As shown in the figure, a sensor which constitutes a sensing apparatus in accordance with this example comprises a waveguide 102 of a microstrip line type consisting of a conductor 102a, a ground conductor 102b, and a dielectric 105. In the figure, reference numeral 2101 denotes an object to be analyzed or identified. Further, in this example, as the method of coupling an electromagnetic wave 104 into the waveguide 102, an antenna structure which is not shown is provided at a part of the waveguide 102. However, the present invention is not limited to use of such method, and, as described above, a method of connecting an active element for generating a desired electromagnetic wave to a part of a waveguide or a method of connecting a waveguide to an external circuit through which an electromagnetic wave propagates by means of a connector may also be used. Alternatively, coupling may be made by using a diffraction grating or a similar element or by utilizing a surface plasmon resonance technique.

The sensor structure in accordance with this example is basically identical to the sensor structure described in Example 1, so that detailed description of the respective portions are omitted below. In the above-described sensor structures, an object is periodically disposed. However, the sensor structure in accordance with this example is not limited to the periodic arrangement, and, for example, as shown in FIG. 21, the object 2101 is disposed such that the interval of disposition varies locally. In this example, a part of pieces of the object which are to be originally disposed at an interval of 50 μm. is omitted and thus the interval between adjacent pieces of the object is locally 100 μm. This means that a defect is incorporated into a part of the periodic disposition structure. However, the discrete disposition manner is not limited to the above. It is sufficient that the periodicity of disposition of the object is partially disturbed, such as a case where the disposition amount of a part of the object is changed from that of the other part. Further, a factor of disturbing the periodicity is not necessarily provided. In such a case, as a consequence, the object is periodically disposed as described in the above examples.

Figure 22:
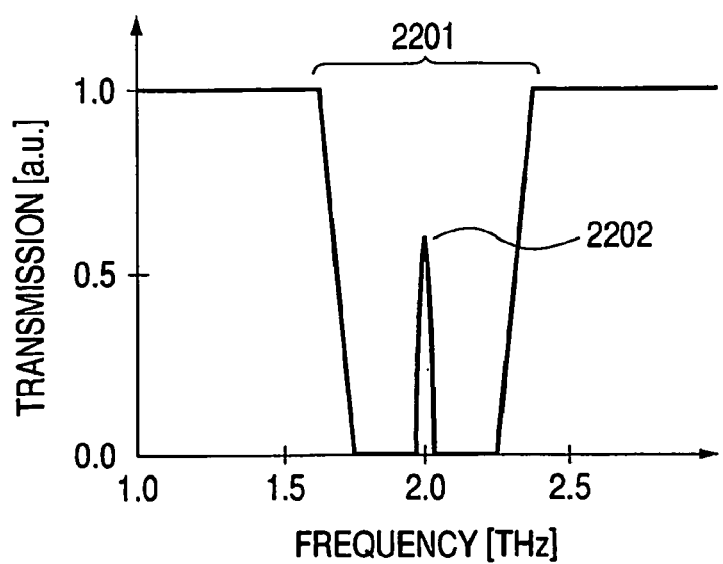
FIG. 22 is a graphical representation explaining a mechanism for an operation of a sensor in accordance with Example 4.

FIG. 22 is a graphical representation explaining a mechanism for an operation of a sensor having such disposition of an object. In general, when a factor of disturbing the periodicity is present in a part of the periodic arrangement as in this example, there is locally present, in a bandgap which is a non-transmissive region 2201 of an electromagnetic wave, a transmissive region 2202 through which the electromagnetic wave passes. The transmissive region 2202 can be controlled by the discrete disposition manner. Further, it is expected that the transmissive region 2202 changes depending on the physical properties of the object. In the aforementioned examples, the object is analyzed or identified on the basis of an amount of shift of a bandgap or a amount of attenuation. However, in this example, the object can be analyzed or identified by a change of the local transmissive region 2202. Because the transmissive region 2202 is locally present in the non-transmissive region 2201, the Q-value is high. Therefore, there is obtained an effect that the S/N ratio of a signal is improved, thereby making it possible to analyze or identify an object with a high sensitivity.

This application claims priority from Japanese Patent Application No. 2004-315839 filed on Oct. 29, 2004, which is hereby incorporated by reference herein.

The invention claimed is:

1. A sensor comprising:
    a waveguide comprising a substrate and a conductor provided on the substrate, for transmitting an electromagnetic wave having at least a part of frequency band of 30 GHz to 30 THz; and
    a plurality of protrusions provided on the conductor,
    wherein the plurality of protrusions are provided in a propagation direction of the electromagnetic wave and provided periodically at an interval which is about a half of a wavelength of the electromagnetic wave.

2. The sensor according to claim 1,
    wherein a plurality of conductors are provided on the substrate, each of the conductors provided with a plurality of protrusions, and
    wherein an electromagnetic wave can propagate through each of the conductors.

3. A sensing apparatus comprising:
    the sensor set forth in claim 1;
    a detecting portion for detecting the electromagnetic wave which has interacted with the object at the plurality of protrusions and propagated through the waveguide; and
    a storage portion for storing information associated with a property of the object,
    wherein the information obtained by the detecting portion and the information stored in the storage portion are used to analyze or identify the property of the object.

4. A sensing apparatus comprising:

the sensor set forth in claim 1; and means for coupling the electromagnetic wave into the waveguide for allowing the electromagnetic wave to propagate therethrough.

5. The sensor according to claim 1, wherein the waveguide is a coplanar waveguide which comprises a dielectric having disposed on a surface thereof the single conductor and a ground conductor with a minute gap between the single conductor and the ground conductor, and wherein the protrusions are disposed on the surface of the dielectric and have a structure in which the object is disposed in the minute gap at a pitch corresponding to a half of the wavelength of the electromagnetic wave.

6. A sensing apparatus comprising the sensor set forth in claim 1, further comprising:

a detecting portion for detecting the electromagnetic wave which has propagated through the waveguide, wherein a plurality of the objects disposed at each of the plurality of protrusions and an electromagnetic wave propagating through the waveguide interact with each other, and wherein the electromagnetic wave subjected to the interaction is detected by the detecting portion.

7. The sensor according to claim 1, wherein the protrusion comprises a dielectric, wherein the waveguide comprises a microstrip line comprising a single conductor, and wherein the propagation direction of the electromagnetic wave is defined by the conductor.

8. The sensing apparatus according to claim 6, comprising:

an ink jet system for ejecting the plurality of objects toward the plurality of protrusions; and a storage portion for storing information associated with properties of the objects, wherein information obtained by the detecting portion and the information stored in the storage portion are used to analyze or identify the properties of the objects.

9. A sensing apparatus comprising:

a coplanar waveguide comprising a substrate, a conductor provided on the substrate, and a ground conductor provided on the substrate so as to have a minute gap between the conductor and the ground conductor, the waveguide for transmitting an electromagnetic wave having at least a part of a frequency band of 30 GHz to 30 THz;

a detecting portion for detecting an electromagnetic wave which has propagated through the waveguide; and an ink jet system for ejecting a plurality of objects toward the minute gap, wherein the conductor and the ground conductor are disposed on a same surface of the substrate, wherein the minute gap is provided in a propagation direction of the electromagnetic wave, and wherein the plurality of objects can be disposed at an interval corresponding to a half of an wavelength of the electromagnetic wave in the minute gap in the substrate.

* * * * *